(12) United States Patent
Feke et al.

(10) Patent No.: US 7,630,072 B2
(45) Date of Patent: Dec. 8, 2009

(54) FLUORESCENCE CALIBRATOR FOR MULTIPLE BAND FLAT FIELD CORRECTION

(75) Inventors: Gilbert Feke, Glastonbury, CT (US); Douglas L. Vizard, Durham, CT (US)

(73) Assignee: Carestream Health, Inc., Rochester, NY (US)

( * ) Notice: Subject to any disclaimer, the term of this patent is extended or adjusted under 35 U.S.C. 154(b) by 412 days.

(21) Appl. No.: 11/765,618

(22) Filed: Jun. 20, 2007

(65) Prior Publication Data
US 2008/0314114 A1 Dec. 25, 2008

(51) Int. Cl.
*G01J 1/10* (2006.01)
(52) U.S. Cl. .................................. 356/243.1
(58) Field of Classification Search .... 356/243.1–243.8
See application file for complete search history.

(56) References Cited

U.S. PATENT DOCUMENTS

| | | | |
|---|---|---|---|
| 5,799,773 A | | 9/1998 | Heffelfinger et al. |
| 6,002,482 A | * | 12/1999 | Rothfritz et al. ......... 356/243.5 |
| 6,242,114 B1 | | 6/2001 | Yamasaki et al. |
| 7,072,036 B2 | | 7/2006 | Jones et al. |
| 2003/0039383 A1 | | 2/2003 | Naghieh et al. |
| 2003/0105195 A1 | | 6/2003 | Holcomb et al. |
| 2006/0208199 A1 | | 9/2006 | Gallagher et al. |

* cited by examiner

Primary Examiner—Michael P Stafira

(57) ABSTRACT

A fluorescence reference plate for a fluorescence spectroscopic instrument is arranged with fluorescent layers having different excitation and emission characteristics. The fluorescent layers are ordered in the form of a stack for providing a flat-field calibration standard over multiple bands of wavelengths.

42 Claims, 4 Drawing Sheets

FLUORESCENCE CALIBRATOR FOR MULTIPLE BAND FLAT FIELD CORRECTION

FIELD OF THE INVENTION

The invention relates to fluorescence imaging, particularly for biological assay mediums containing fluorophores as autofluorescent content or as exogeneous labels associated with selected contents and, in particular, to calibrating such instrumentation with a fluorescence reference having uniform or otherwise spatially defined fluorescence properties.

BACKGROUND OF THE INVENTION

Fluorescence imaging provides a powerful tool for identifying and characterizing selected contents of assay mediums, particularly biological assays containing in vivo or in vitro contents of interest. Specific molecular structures, including individual proteins or nucleic acids, and cell types or tissues in the form of single or array-based assay mediums can be targeted to fluoresce for identification or characterization.

Within typical fluorescence spectroscopic instruments, the assay mediums are (a) irradiated at predetermined wavelengths that excite fluorophores associated with the selected contents and (b) imaged onto detector arrays for capturing the resulting Stokes-shifted luminescence. Information concerning the spectral content, polarization, intensity, lifetime, distribution, and shape of the luminescent targets over spatial and temporal dimensions can be extracted for identifying or characterizing the selected contents.

Systematic errors arise from spatial non-uniformities associated with both the irradiation and imaging of the assay mediums. For example, two-dimensional assays generally require uniform irradiance over the field of view of the assay medium. The requirements for uniform irradiance can include not only uniform intensity over the field but also uniform spectral content, polarization, angular profile (field pattern), and dose (integrated flux) throughout the field. Systematic errors can arise as field anisotropies among these requirements for uniform irradiance. Systematic errors associated with imaging include optical aberrations such as field curvature, distortion, and chromatic aberration, as well as detection errors such as absorbance errors, dark field error, and variations in detection efficiency. Stray radiation can also influence baseline values.

Calibration techniques for the fluorescence spectroscopic instruments have been applied to quantify and compensate for non-uniformities and other systematic errors associated with the irradiation and imaging of the assays. For example, reference plates containing fluorescent material uniformly distributed throughout the plates have been irradiated and imaged in place of the assay mediums to detect anisotropies or other deviations from expectations. The reference plates occupy the same or an enlarged area of the field of view as the array mediums intended for evaluation and respond to incident light in the same way throughout the occupied area of the field. Any spatial deviations in the fluorescence response, i.e., the fluorescent emission of light at Stokes-shifted wavelengths, are attributable to disparities in the irradiation. The fluorescence response itself is subject to further variation as imaged onto a detector array. The end result is one or more digital images within which deviations from a norm are indicative of errors or other anomalies of the irradiation and imaging systems.

The information acquired from reference plates can be used to (a) correct or otherwise adjust the irradiation and illumination systems, (b) scale the results to a known standard, or (c) provide a baseline for distinguishing systematic variations in the results from true differences within sample assays. For example, fluorescent images of the sample assay mediums can be normalized to fluorescent images of the reference plates having predefined responses.

Many applications require the simultaneous study of different contents within the assay mediums, such as multiple proteins or protein states (e.g., phosphorylation). Unique fluorescent tags that emit different wavelengths upon excitation are associated with the different contents. Different wavelength emitting fluorescent tags excited by the same wavelength are particularly useful for comparing the contents simultaneously. However, different wavelength emitting fluorescent tags excited by different wavelengths provide more flexibility for separate analyses of the contents.

Known reference plates for calibrating fluorescence spectroscopic instruments are generally formed by a coated substrate, a gel plate, or solid film containing one or more fluorescent agents. Some such plates have included multiple fluorescent agents, which can differ depending upon the particular fluorescent tags or probes intended for use within the assay medium. However, combinations of fluorescent agents with overlapping excitation and emission wavelengths can produce interactions that obscure the individual contributions of fluorescent agents. The wavelengths emitted by a first fluorescent agent can be absorbed and hence excite a second fluorescent agent, which diminishes the contribution of the first fluorescent agent and amplifies the contribution of the second fluorescent agent.

SUMMARY OF THE INVENTION

The invention in one or more of its preferred embodiments features a fluorescence reference as a calibrating datum for fluorescence spectroscopic instruments having optical systems for directing fluorescent emissions from epi-illuminated assays onto detector arrays. The fluorescence reference, which can be substituted in place of the assays, contains multiple fluorescent agents over a range of excitation and emission wavelengths. The fluorescence agents are separated into layers with uniform distributions, and the layers are ordered in the form of a stack so that fluorescent agents with emission wavelengths that excite other fluorescent agents are located closer to both a source of illumination and the imaging system (i.e., in the shallower layers) than the other fluorescent agents that are excited by the emission wavelengths. Thus, the fluorescent emissions from fluorescent agents within any given layer do not appreciably excite fluorescent agents in any intervening layers en route to the detector array. As a result, the fluorescent emissions within the numerical aperture of the imaging system can reach the detector array without being diminished by absorption through fluorescent agents of intervening layers.

The fluorescence reference with ordered layers of fluorescent agents can be used to calibrate fluorescence spectroscopic instruments through overlapping ranges of excitation and emission wavelengths. Calibrations can be conducted over the intended excitation and emission ranges of the fluorescence spectroscopic instruments or can be matched to the particular excitation and emission properties of fluorescent tags or autofluorescent contents of assays intended for study. Each layer of the fluorescence reference covers a different spectral band of excitation and emission wavelengths, and the multiple layers can be assembled to calibrate the fluorescence spectroscopic instruments over a wide range of intended use.

The layers of fluorescent agents are preferably ordered with respect to both absorbance and transmission characteristics. Each layer has an absorbance band that includes the wavelengths that excite the fluorescent agents within the layer and a transmission band that includes not only the wavelengths emitted by the fluorescent agents within the layer but also the wavelengths required for exciting and transmitting emissions from the fluorescent agents within deeper layers (i.e., layers more remote from the imaging system).

For typical Stokes-shifting fluorescent agents, the ordered layers can be arranged to function as a succession of band-stop filters that attenuate wavelength bands that progressively shift toward higher wavelengths with increasing depth. Both the excitation and the emission wavelengths of the fluorescent agents in successively deeper layers shift toward the longer wavelengths so that the desired excitation wavelengths reach the deeper fluorescent agents and the emission wavelengths from the fluorescent agents reach the imaging system. Other attenuation patterns, such as band-stop patterns, can be used for other combinations of fluorescent agents having excitation and emission wavelengths that vary somewhat differently in progression. The attenuation bands for successive layers provide a cumulative attenuating effect for the deeper layers.

One version of the invention as a fluorescence reference for fluorescence spectroscopic instruments includes a plurality of fluorescent agents with overlapping excitation and emission wavelengths separated into layers and ordered in the form of a stack. The fluorescent agents with emission wavelengths that excite other of the fluorescent agents are located closer to the top of the stack (i.e., the shallower layers) than the other fluorescent agents that are excited by the emission wavelengths.

In a preferred embodiment for measuring spatial non-uniformities over a range of overlapping excitation and emission wavelengths, the fluorescent agents within individual layers of the stack are uniformly distributed throughout the individual layers, and the individual layers are uniformly transmissive throughout a common spatial extent. A majority of the fluorescent emissions from the fluorescent agents of layers closer to the bottom of the stack (i.e., the deeper layers) transmit to the top of the stack without being diminished by fluorescent encounters (absorption) with the fluorescent agents of layers closer to the top of the stack (i.e., the shallower layers). Each of at least three layers of the fluorescence reference covers different spectral bands of excitation and emission wavelengths, and the emission wavelengths increase between layers approaching the bottom of the stack.

A first of the layers can have an absorbance band that absorbs wavelengths that excite the fluorescent agents within the first layer and a transmission band that transmits wavelengths emitted by the fluorescent agents within the first layer as well as wavelengths required for exciting and transmitting emissions from the fluorescent agents within a second of the layers closer to the bottom of the stack. For example, the layers can be arranged as a succession of band-stop filters that attenuate wavelength bands that progressively shift toward higher wavelengths approaching the bottom of the stack. The excitation wavelengths of the fluorescent agents in succeeding layers counted from the top of the stack preferably shift toward longer wavelengths so that the excitation wavelengths reach the fluorescent agents in the layer closest to the bottom of the stack. The emission wavelengths of the fluorescent agents in succeeding layers counted from the top of the stack also preferably shift toward longer wavelengths so that the emission wavelengths of the fluorescent agents in the layer closest to the bottom of the stack transmit through the top of the stack.

Diffuse interfaces can be formed between the layers of the stack for reducing interference effects between the layers. For example, the diffuse interfaces can be formed by intervening layers that separate the layers containing fluorescent agents. The layers themselves can be formed by resin substrates within which the fluorescent agents are embedded in the form of dyes. Cover layers can be laminated to opposite sides of the resin substrates.

As an alternative to the diffuse interfaces, a refractive-index-matching material can be placed between adjacent layers for reducing interference effects between the layers. The refractive-index-matching material can comprise a refractive-index matching adhesive.

An opaque layer is preferably appended to the bottom of the stack to prevent stray light from entering the stack. The opaque layer can be formed by a diffusely reflective material for redirecting emissions from the fluorescent agents toward the top of the stack. A rigid transmissive substrate can be appended to the top of the stack. Preferably, the rigid transmissive substrate is made of anti-reflective glass.

Another version of the invention involves a system for calibrating a fluorescence spectroscopic instrument having an optical system for directing fluorescent emissions from an epi-illuminated assay onto a detector array. A fluorescence reference has a top and bottom. A plurality of layers is formed within the fluorescence reference. Fluorescent agents within each of the layers have predetermined excitation and emission wavelengths. The top of the fluorescent reference is transmissive for exposing the plurality of layers to the excitation wavelengths of the fluorescent agents and for conveying the emission wavelengths of the fluorescent agents en route to the detector array. The emission wavelengths of a first of the fluorescent agents correspond to the excitation wavelengths of a second of the fluorescent agents. The layer containing the first fluorescent agent is located closer to the top of the fluorescent reference than the layer containing the second fluorescent agent.

Preferably, the emission wavelengths of a third fluorescent agent correspond to the excitation wavelengths of at least one of the first and second fluorescent agents. The layer containing the third fluorescent agent is located more remote from the top than the layers containing the first and second fluorescent agents. For conventional Stokes-shifting fluorescent agents, the excitation wavelengths of fluorescent agents within successive layers increase approaching the bottom of the fluorescence reference. Similarly, the emission wavelengths of fluorescent agents within successive layers increase approaching the bottom of the fluorescence reference.

A first of the layers can have an absorbance band that absorbs wavelengths that excite the first fluorescent agents within the first layer and a transmission band that transmits wavelengths emitted by the first fluorescent agents within the first layer as well as wavelengths required for exciting and transmitting emissions from the second fluorescent agents within a second of the layers closer to the bottom of the stack. For example, the layers can be arranged as a succession of band-stop filters that attenuate wavelength bands that progressively shift toward higher wavelengths approaching the bottom of the stack.

Diffuse interfaces or refractive-index-matching material can be interleaved between the layers of the fluorescent reference. The layers themselves can have resin substrates within which the fluorescent agents are embedded in the form of dyes. An opaque diffusely reflective layer can be appended to the bottom of the fluorescence reference, and a rigid transmissive substrate can be appended to the top of the stack.

Another version of the invention involves a method of assembling a fluorescence reference for calibrating a fluorescence spectroscopic instrument having an optical system for directing fluorescent emissions from an epi-illuminated assay onto a detector array. A plurality of layers containing uniformly distributed fluorescent agents having overlapping excitation and emission wavelengths are arranged into a stack. The layers are ordered from top to bottom of the stack so that the fluorescent agents with emission wavelengths that excite other of the fluorescent agents are located closer to the top of the stack than the other fluorescent agents that are excited by the emission wavelengths.

The layers can be arranged as a succession of band-stop filters attenuating wavelengths that progressively shift toward higher wavelengths approaching the bottom of the stack. Preferably, at least three layers containing uniformly distributed fluorescent agents are ordered within the stack. Either or both of the excitation wavelengths and the emission wavelengths of the fluorescent agents can be shifted toward longer wavelengths approaching the bottom of the stack.

DETAILED DESCRIPTION OF THE INVENTION

Figure 1:
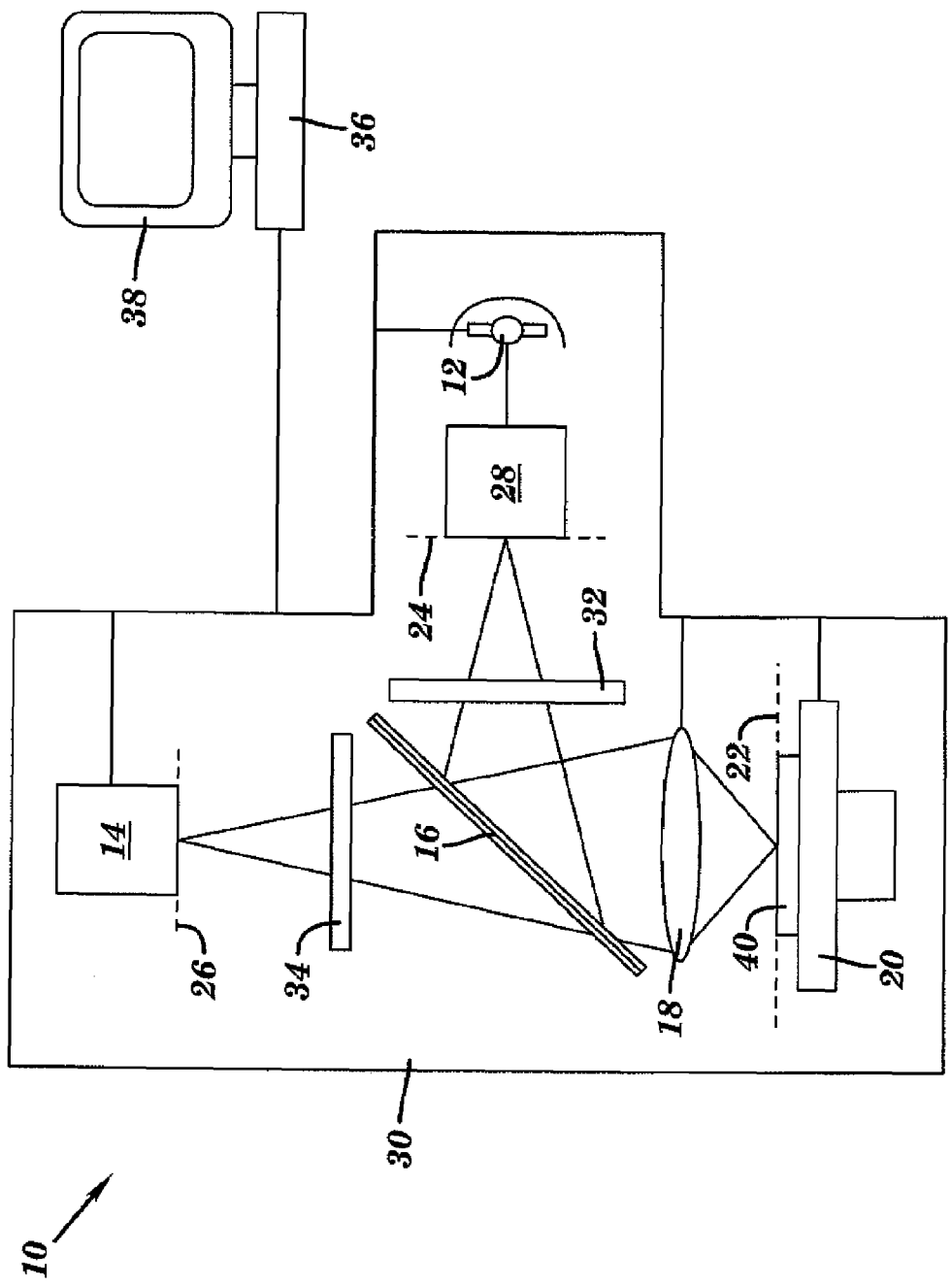
FIG. 1 is a diagram of a fluorescence spectroscopic instrument having an optical system for directing fluorescent emissions from an epi-illuminated fluorescence reference onto a detector array.

The following is a detailed description of the preferred embodiments of the invention, reference being made to the drawings in which the same reference numerals identify the same elements of structure in each of the several figures.

A fluorescence spectroscopic instrument 10 compatible with the invention is shown in FIG. 1 including a light source 12 capable of producing a range of excitation wavelengths and a detector array 14 capable of detecting relative intensities of a range of emission wavelengths. A beamsplitter 16 connects both the light source 12 and the detector array 14 to a common imaging system 18 that is focused above a sample stage 20. The entire light path originating at the light source 12, traversing the sample stage 20 (albeit converted to other wavelengths), and ending at the detector array 14 is fully enclosed within a light-tight housing 30 or other enclosure, which prevents stray light from entering the light path or otherwise reaching the detector array 14. The environment within the housing 30 can be controlled to optimize or stabilize conditions such as temperature, humidity, and gas content.

The imaging system 18, which can provide magnification or reduction, couples a conjugate plane 22 of the sample stage 20 to both a conjugate plane 24 at the output of an illuminator 28 and another conjugate plane 26 of the detector array 14. The illuminator 28 produces an illuminated field at the conjugate plane 24, which is relayed by the imaging system 18 to the conjugate plane 22 above the sample stage 20. Filters 32 and 34 between the beamsplitter 16 and each of the light source 12 and the detector array 14 separately control the bands of excitation and emission wavelengths.

The light source 12 can be an arc lamp, such as a xenon arc lamp, or other multi-wavelength (e.g., white light) source operating through a range of wavelengths, particularly visible wavelengths but also including ultraviolet or infrared wavelengths. One such operating range capable of exciting known fluorescent tags spans a range from 390 nanometers to 770 nanometers. The illuminator 28 produces an irradiance field at the conjugate output plane 24, which is relayed by the imaging system 18 to the conjugate plane 22 of the sample stage 20 for irradiating sample assays by epi-illumination. The filter 32, which can be a dielectric filter, passes light within the intended excitation band but blocks other wavelengths not intended for study. A set of different filters can be used to cover other excitation bands.

The detector array 26 can be a charge coupled device (CCD) array or other detector arrangement capable of detecting relative intensities of excitation wavelengths intended for study. For example, emissions from many fluorescent tags can be captured within a wavelength range from 480 nanometers to 830 nanometers. Images can be captured by the detector array 26 in various exposure formats, such as single or multiple exposures, progressive exposures, or time-lapse exposures and can be further processed by an associated computer 36, such as for color-coding or other formatting, and displayed on an associated monitor 38. The images collected from one sample assay can be stored and compared to other images collected from a fluorescence reference plate 407 which is mounted on the sample stage 20 in place of a sample assay for purposes of calibration.

The filter 34, which can also be a dielectric filter or one of a set of dielectric filters, passes light within the monitored emission band but blocks other wavelengths not intended for study. The beamsplitter 16 can be both partially reflective for directing light from the light source 12 to the fluorescence reference plate 40 or sample assay and partially transmissive for directing light from the fluorescence reference plate 40 or sample assay to the detector array 14. The imaging system 18 can include zoom and focus controls to adjust the field of view of the imaging system to match the dimensions of the fluorescence reference plate 40 or sample assay.

Figure 2:
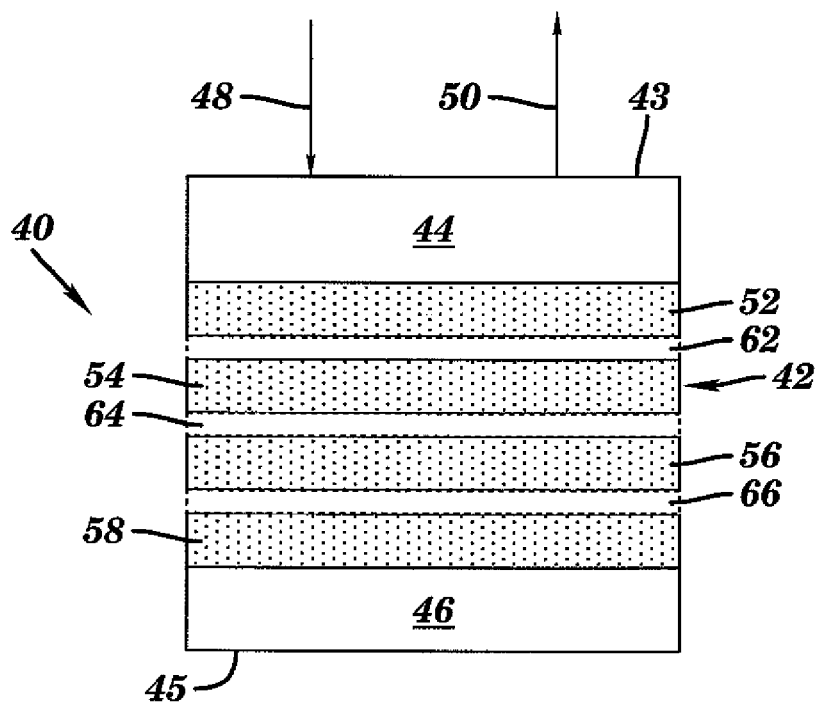
FIG. 2 is an enlarged cross-section through a portion of the fluorescence reference showing individual layers in the form of a stack.

The fluorescence reference plate 40 as envisioned for one embodiment of the invention is depicted in FIG. 2 in the form of a stack 42. At the top 43 of the stack 42 is an anti-reflective glass plate 44 that allows filtered incident light 48 from the light source 12 to enter the stack 42 and allows Stokes-shifted light 50 emitted by fluorescent agents within the plate 40 to exit the stack 42. At the bottom 45 of the stack 42 is an opaque diffusely reflective sheet 46 that blocks stray light from entering the stack 42. Both the anti-reflective plate 44 and the opaque diffusely reflective sheet 46 are arranged to avoid specular reflections that could produce interference effects within the stack 42.

Four different fluorescent layers 52, 54, 56 and 58 in the form of resin sheets embedded with uniformly distributed fluorescent agents are ordered within the stack 42 in accordance with the spectral excitation and emission characteristics of the fluorescent agents. Generally, the fluorescent layers 52, 54, 56 and 58 are ordered so that the excitation and emission wavelengths of the fluorescent agents progressively increase from the top 43 to the bottom 45 of the stack 42. Intervening film layers 62, 64, and 66, which are preferably formed with diffuse surfaces such as by matting, inhibit specular reflections between the fluorescent layers 52, 54, 56, and 58 to avoid interference effects such as Newton's rings.

Since fluorescence involves the absorption of the excitation wavelengths in advance of emitting other (usually longer) wavelengths, each of the fluorescent layers acts as a band-stop filter that blocks the further transmission of the absorbed wavelengths. Using conventional Stokes-shifting fluorescent agents whose emission wavelengths are longer than their excitation wavelengths, the fluorescent layers are ordered so that the lowest wavelengths are blocked by the topmost layer, and the next lowest wavelengths are blocked by succeeding layers, which has the effect of enlarging the range of wavelengths that are blocked from reaching fluorescent layers closer to the bottom 45 of the stack 42. Since the excitation wavelengths of the fluorescent agents in bottommost fluorescent layer 58 are higher than the excitation wavelengths of fluorescent agents in all three overlying fluorescent layers 52, 54, and 56, the enlarged range of wavelengths blocked from reaching the bottom fluorescent layer 58 does not include the intended excitation wavelengths of the bottom fluorescent layer 58. Thus, despite the progressively enlarging range of attenuation from the top 43 to the bottom 45 of the stack 42, each succeeding fluorescent layer 52, 54, 56, and 58 can be epi-illuminated with its intended excitation wavelength.

The order of the fluorescent layers 52, 54, 56, and 58 also prevents the extinction of emitted Stokes-shifted wavelengths from the deeper fluorescent layers by the absorption or excitation of the wavelengths within the shallower layers. The excitation wavelengths of the overlying fluorescent layers are lower than both the excitation and emission wavelengths of the underlying fluorescent layers. Thus, the overlying fluorescent layers do not absorb or otherwise block via the mechanism of fluorescence the transmission of fluorescent emissions from the underlying fluorescent layers en route to the detector array 14. However, the fluorescent emissions of the shallower layers can be used to excite further emissions in the deeper layers to at least partially compensate for transmission losses between the layers.

Figure 3:
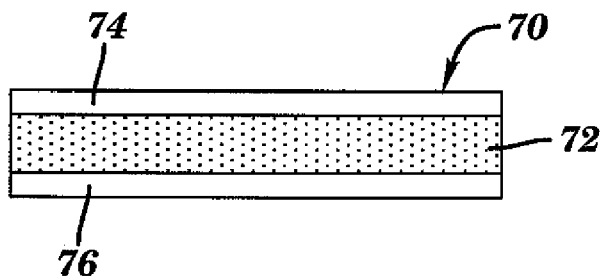
FIG. 3 is a similarly enlarged cross-sectional view of a single layer embedded with fluorescent agents and sandwiched between two transparent covers.

The fluorescent layers 52, 54, 56, and 58 can be formed in a variety of ways. For example, a fluorescent layer 70 shown in FIG. 3 includes a core 72 formed by a combination of resin (e.g., polycarbonate) and dyes extruded together under heat and pressure. Clear film layers 74 and 76 on opposite sides of the core 72 resist migration of the fluorescent agents from the core 72. Alternatively, a clear polyester base could be deep dyed within a heated bath. The dye molecules are entrapped within the polyester base as the base is cooled. Dye solutions can also be coated onto one or both sides of a clear resin base such as a polyester film. In the latter case, each base sheet supports two fluorescent layers. The preferred fluorescent layers 52, 54, 56, and 58 each have a thickness of between 0.036 millimeters and 0.127 millimeters and are made of polycarbonate or polyester resin.

Examples of such fluorescent films and laminates are available from Rosco Laboratories Inc. of Stamford, Conn. under the trade name ROSCOLUX filters. A combination of four ROSCOLUX filters for creating an ordered arrangement of fluorescent layers is set forth in the table below:

| Fluorescent Layer (from top to bottom) | ROSCOLUX Part No. | Cut-on* (wavelength in nm) | Fluorescence Band (wavelength in nm) |
|---|---|---|---|
| 52 | 96 | 480 | 480-600 |
| 54 | 18 | 620 | 600-670 |
| 56 | 4960 | 660 | 670-750 |
| 58 | 4390 | NA | 759-830 |

*where transmission above the cut-on wavelength is >70% and drops sharply below the cut-on wavelength.

Figure 4:
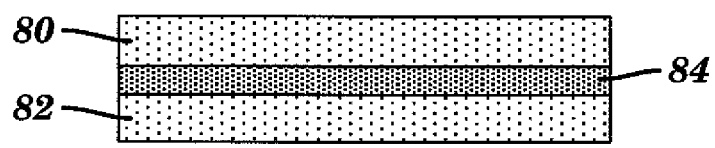
FIG. 4 is a similarly enlarged cross-sectional view of two layers embedded with fluorescent agents bonded together by an index-matching adhesive.

As shown in FIG. 4, adjacent fluorescent layers 80 and 82 are separated by an index-matching adhesive layer 84 that joins the fluorescent layers 80 and 82 together without producing a refractive interface between the layers 80 and 82. For example, epoxy resins can be used for this purpose. The index-matching adhesive layer 84 can be replicated for replacing the intervening film layers 62, 64, and 66 in the fluorescent reference plate 40 of FIG. 2. Instead of reducing specular reflection by diffusion, the index-matching layers 84 reduce refractive index differences across material interfaces that otherwise support such reflections.

Figure 5:
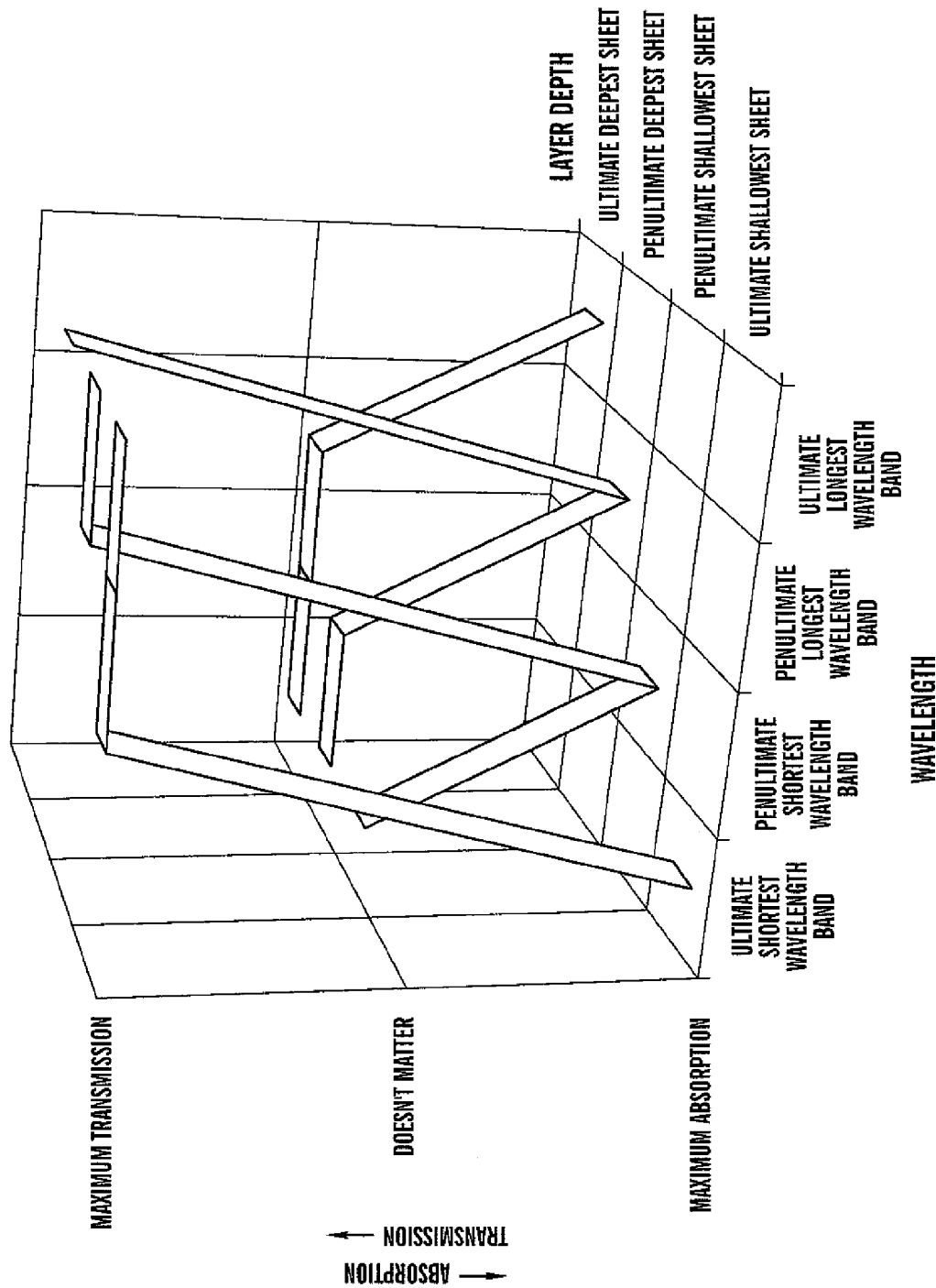
FIG. 5 is a three-axis graph relating variations in absorption of different excitation wavelength bands through different layers of the stack.
Figure 6:
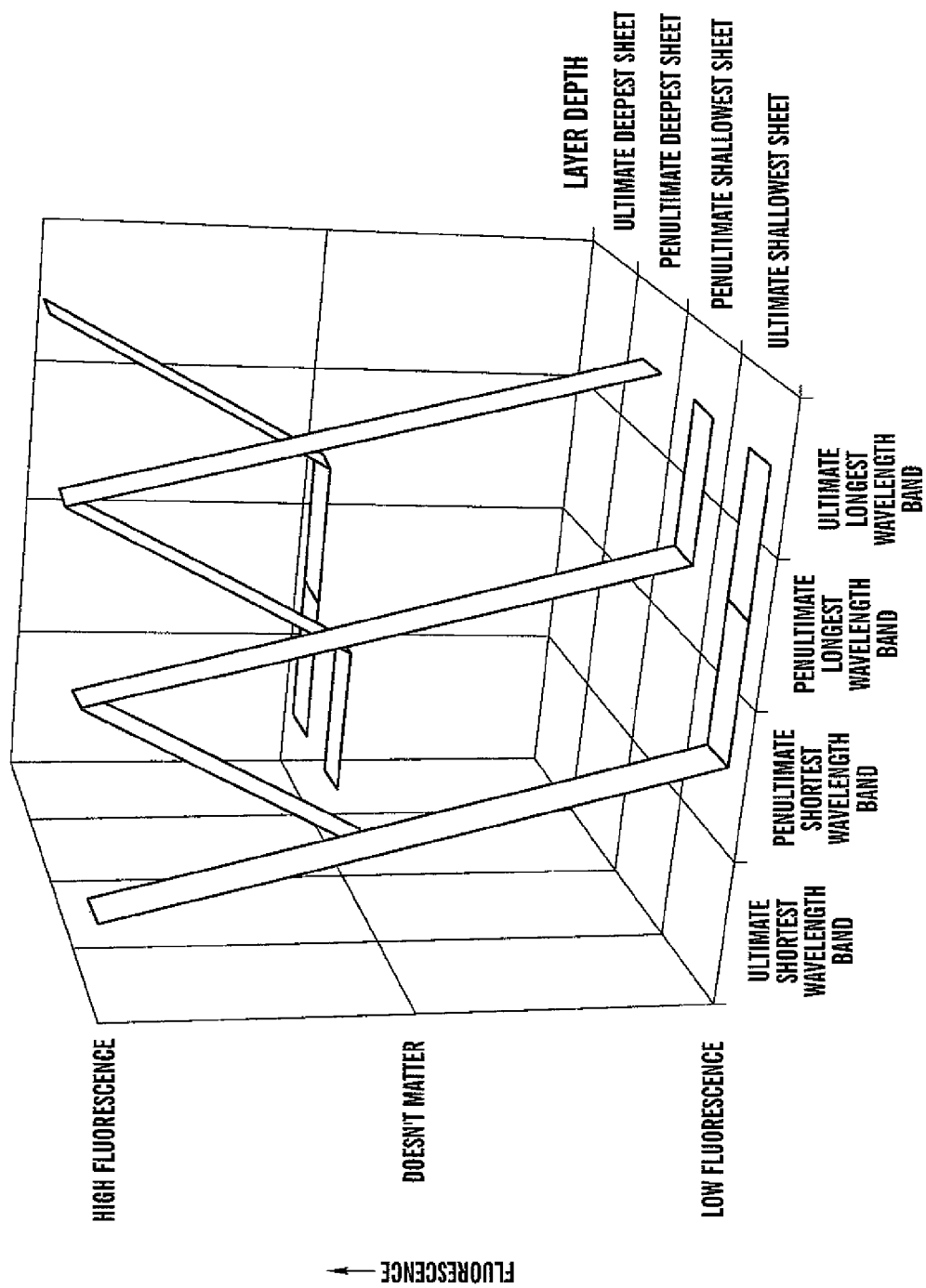
FIG. 6 is a three-axis graph relating variations in fluorescence of different emission wavelength bands through the different layers of the stack.

The three-dimensional graphs of FIGS. 5 and 6 distinguish the different fluorescent layers over various excitation and emission bands as measured by absorption/transmission or fluorescence. As shown in the graph of FIG. 5, the ultimate shallowest layer (sheet) absorbs only the ultimate shortest wavelength band, the penultimate shallowest layer (sheet) absorbs only the penultimate shortest wavelength band, the penultimate deepest layer (sheet) absorbs only the penultimate shortest wavelength band, and the ultimate deepest layer (sheet) absorbs only the ultimate shortest wavelength band. However, under conditions of epi-illumination, the effects of the absorption are cumulative from the shallowest to the deepest layers (sheets). For example, both the ultimate shortest wavelength band and the penultimate shortest wavelength band are blocked from reaching the penultimate deepest layer (sheet), by the absorption characteristics of the overlying ultimate shallowest layer (sheet) and the penultimate shallowest layer (sheet).

Although offset in wavelength, the fluorescence characteristics of the fluorescent layers are substantially complementary to the absorption characteristics of the same layers. As shown in FIG. 6, the ultimate shallowest layer (sheet) fluoresces at the ultimate shortest wavelength band, the penultimate shallowest layer (sheet) fluoresces at only the penultimate shortest wavelength band, the penultimate deepest layer (sheet) fluoresces at the penultimate shortest wavelength band, and the ultimate deepest layer (sheet) fluoresces at the ultimate shortest wavelength band. Since the progressively deeper layers (sheets) fluoresce at progressively longer wavelength bands, the absorption characteristics (see preceding graph) of the overlying layers (sheets) do not block the transmission of the fluorescent bands through the overlying layers to the imaging system 18, which, within the bounds of its numerical aperture, collects fluorescent emissions from the fluorescent reference plate 40.

The fluorescent agents considered for filling the fluorescent layers of the preceding examples are all conventional Stokes-shifting fluorescent agents that convert shorter excitation wavelengths into longer fluorescence wavelengths. However, other fluorescent agents are known that fluoresce at shorter wavelengths than their excitation wavelengths. A stack of ordered fluorescent layers can still be used in accordance with the invention by absorbing the ultimate longest wavelength band with the ultimate shallowest layer, absorbing the penultimate longest wavelength band with the penultimate shallowest layer, absorbing the penultimate shortest wavelength band with the penultimate deepest layer, and absorbing the ultimate shortest wavelength band with the ultimate deepest layer.

Preferably, the fluorescent layers (e.g., 52, 54, 56, and 58) have a length and width sufficient to cover the field of view of the imaging system 18, and the fluorescence emissions from each layer are spatially uniform across the length and width of the layers providing a flat field for the imaging system 18. In this regard, the transmission characteristics of each fluorescent layer and any intervening non-fluorescent sheets as well as the anti-reflective glass plate 44 are also spatially uniform throughout the field of view.

The total thickness of the stack 42 is preferably within the depth of focus of the imaging system 18. The fluorescent layers can be rigid or flexible. However, both the anti-reflective glass plate 44 and the opaque diffusely reflective sheet 46 are preferably rigid to hold the fluorescent layers in place. A frame or other clamping device (not shown) can be used to secure the entire stack 42. Although depicted with four fluorescent layers, more or less fluorescent layers can be use to provide the desired range of calibration or for other purposes.

The stack 42 of the illustrated embodiment is referred to as having a top 43 and a bottom 44. However, the stack 42 can be oriented in any direction including topside down with the understanding that incident light (e.g. from the light source 12) propagates generally from top to bottom of the stack and the exiting light (e.g., en route to the detector array 14) propagates generally from bottom to top of the stack. The shallowest layers remain closest to the top of the stack, and the deepest layers remain closest to the bottom of the stack independently of the overall orientation of the stack.

The opaque diffusely reflective sheet 46 is preferably white and diffusely reflective over the entire useful range of excitation and emission wavelengths. The diffuse reflectivity is also preferably spatially uniform across the effective length and width of the opaque diffusely reflective sheet 46. A matte or other optically diffuse finish can be used to avoid interference effects.

The fluorescence reference plate 40 can be used to perform absolute calibrations where the excitation and emission characteristics of the fluorescence reference plate 40 are known or can provide a reference datum against which measures of different sample assays can be compared or otherwise normalized. The periodic substitution of the fluorescent fluorescence plate 40 for the sample assays can also be used to monitor changes undergone by the fluorescence spectroscopic instrument 10. For example, the condition of the light source 12 can be monitored as well as the introduction of new errors. Preferably, emissions from the fluorescence reference plate 40 are captured under substantially the same conditions with each measurement intended for comparison, including the same excitation and emission wavelength filtration and other system configurations such a focus, zoom, and f-stop.

Although the imaging system 18 of the fluorescence spectroscopic instrument 10 provides an overlapping pathway between the sample stage 20 and both the light source 12 and the detector array 14, entirely separate illumination and detection systems can be used. For example, light from the light source can be conveyed by fiber optics or other separate optical pathways to the sample stage 20 for illuminating the fluorescent reference plate or sample assays from directions that do not interfere with the collection of light by the imaging system.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10—fluorescence spectroscopic instrument
12—light source
14—detector array
16—beam splitter
18—imaging system
20—sample stage
22—conjugate plane (sample stage)
24—conjugate plane (illuminator)
26—conjugate plane (detector)
28—illuminator
30—light-tight housing
32—filter (excitation wavelengths)
34—filter (emission wavelengths)
36—computer
38—monitor
40—fluorescence reference plate
42—stack
43—top of stack
44—anti-reflective glass plate
45—bottom of stack
46—opaque diffusely reflective sheet
48—filtered incident light
50—Stokes-shifted light
52—fluorescent layer (shallowest)
54—fluorescent layer
56—fluorescent layer
58—fluorescent layer (deepest)
62—intervening film layer (shallowest)
64—intervening film layer
66—intervening film layer (deepest)
70—fluorescent layer
72—core
74—clear film layer
76—clear film layer
80—fluorescent layer
82—fluorescent layer
84—index-matching adhesive layer

The invention claimed is:

1. A fluorescence reference for fluorescence spectroscopic instruments comprising:
   a plurality of fluorescent agents with a range of excitation and emission wavelengths being separated into layers and ordered in the form of a stack referenced between a top and bottom; and
   the fluorescent agents with emission wavelengths that excite other of the fluorescent agents being located closer to the top of the stack than the other fluorescent agents that are excited by the emission wavelengths.

2. The fluorescence reference of claim 1 in which the fluorescent agents within individual layers of the stack are uniformly distributed throughout the individual layers, and the individual layers are uniformly transmissive throughout a common spatial extent.

3. The fluorescence reference of claim 1 in which a majority of the fluorescent emissions from the fluorescent agents of layers closer to the bottom of the stack transmit to the top of the stack without being shifted in wavelength by fluorescent encounters with the fluorescent agents of layers closer to the top of the stack.

4. The fluorescence reference of claim 1 in which each of at least three layers of the fluorescence reference covers different spectral bands of excitation and emission wavelengths, and the emission wavelengths increase between layers approaching the bottom of the stack.

5. The fluorescence reference of claim 1 in which a first of the layers has an absorbance band that absorbs wavelengths that excite the fluorescent agents within the first layer and a transmission band that transmits wavelengths emitted by the fluorescent agents within the first layer as well as wavelengths required for exciting and transmitting emissions from the fluorescent agents within a second of the layers closer to the bottom of the stack.

6. The fluorescence reference of claim 5 in which the layers are arranged as a succession of band-stop filters that attenuate wavelength bands that progressively shift toward higher wavelengths approaching the bottom of the stack.

7. The fluorescence reference of claim 6 in which the excitation wavelengths of the fluorescent agents in succeeding layers counted from the top of the stack shift toward longer wavelengths so that the excitation wavelengths reach the fluorescent agents in the layer closest to the bottom of the stack.

8. The fluorescence reference of claim 7 in which the emission wavelengths of the fluorescent agents in succeeding layers counted from the top of the stack shift toward longer wavelengths so that the emission wavelengths of the fluorescent agents in the layer closest to the bottom of the stack transmit through the top of the stack.

9. The fluorescence reference of claim 1 further comprising diffuse interfaces between the layers of the stack for reducing interference effects between the layers.

10. The fluorescence reference of claim 9 in which the diffuse interfaces are formed by intervening layers that separate the layers containing fluorescent agents.

11. The fluorescence reference of claim 1 in which the layers include resin substrates within which the fluorescent agents are embedded.

12. The fluorescence reference of claim 11 in which the layers are formed by laminations in which the resin substrates are sandwiched between transmissive cover layers.

13. The fluorescence reference of claim 11 in which the fluorescent agents are formed by dyes.

14. The fluorescence reference of claim 1 further comprising refractive-index-matching joints between adjacent layers for reducing interference effects between the layers.

15. The fluorescence reference of claim 14 in which the refractive-index-matching joints comprise a refractive-index matching adhesive.

16. The fluorescence reference of claim 1 further comprising an opaque layer at the bottom of the stack to prevent stray light from entering the stack.

17. The fluorescence reference of claim 16 in which the opaque layer is formed by a diffusely reflective material for redirecting emissions from the fluorescent agents toward the top of the stack.

18. The fluorescence reference of claim 1 further comprising a rigid transmissive substrate at the top of the stack.

19. The fluorescence reference of claim 18 in which the rigid transmissive substrate is made of anti-reflective glass.

20. A system for calibrating a fluorescence spectroscopic instrument having an optical system for directing fluorescent emissions from an epi-illuminated assay onto a detector array comprising:
   a fluorescence reference having a top and bottom;
   a plurality of layers within the fluorescent reference;
   fluorescent agents within each of the layers having predetermined excitation and emission wavelengths;
   the top of the fluorescent reference being transmissive for exposing the plurality of layers to the excitation wavelengths of the fluorescent agents and for conveying the emission wavelengths of the fluorescent agents en route to the detector array;
   the emission wavelengths of a first of the fluorescent agents corresponding to the excitation wavelengths of a second of the fluorescent agents; and
   the layer containing the first fluorescent agent being located closer to the top of the fluorescent reference than the layer containing the second fluorescent agent.

21. The system of claim 20 in which the emission wavelengths of a third fluorescent agent correspond to the excitation wavelengths of at least one of the first and second fluorescent agents.

22. The system of claim 21 in which the layer containing the third fluorescent agent is located more remote from the top than the layers containing the first and second fluorescent agents.

23. The system of claim 22 in which the excitation wavelengths of fluorescent agents within successive layers increase approaching the bottom of the fluorescence reference.

24. The system of claim 22 in which the emission wavelengths of fluorescent agents within successive layers increase approaching the bottom of the fluorescence reference.

25. The system of claim 20 in which a first of the layers has an absorbance band that absorbs wavelengths that excite the first fluorescent agents within the first layer and a transmission band that transmits wavelengths emitted by the first fluorescent agents within the first layer as well as wavelengths required for exciting and transmitting emissions from the second fluorescent agents within a second of the layers closer to the bottom of the stack.

26. The system of claim 25 in which the layers are arranged as a succession of band-stop filters that attenuate wavelength bands that progressively shift toward higher wavelengths approaching the bottom of the stack.

27. The system of claim 20 further comprising diffuse interfaces between the layers of the fluorescent reference.

28. The system of claim 27 in which the diffuse interfaces are formed by intervening layers that separate the layers containing fluorescent agents.

29. The system of claim 20 in which the layers include resin substrates within which the fluorescent agents are embedded in the form of dyes.

30. The system of claim 20 further comprising refractive-index-matching joints between adjacent layers.

31. The system of claim 30 in which the refractive-index-matching joints comprise a refractive-index matching adhesive.

32. The system of claim 20 further comprising an opaque diffusely reflective layer at the bottom of the fluorescence reference.

33. The system of claim 20 further comprising a rigid transmissive substrate at the top of the stack.

34. The system of claim 20 in which the fluorescent agents are uniformly distributed throughout the individual layers, and the individual layers are uniformly transmissive throughout a common spatial extent.

35. A method of assembling a fluorescence reference for calibrating a fluorescence spectroscopic instrument having an optical system for directing fluorescent emissions from an epi-illuminated assay onto a detector array comprising steps of:
- arranging a plurality of layers containing uniformly distributed fluorescent agents having a range of excitation and emission wavelengths into a stack; and
- ordering the layers from top to bottom of the stack so that the fluorescent agents with emission wavelengths that excite other of the fluorescent agents are located closer to the top of the stack than the other fluorescent agents that are excited by the emission wavelengths.

36. The method of claim 35 in which the step of ordering includes arranging the layers as a succession of band-stop filters that attenuate wavelength bands that progressively shift toward higher wavelengths approaching the bottom of the stack.

37. The method of claim 35 in which the step of ordering includes ordering at least three layers, and at least one of (a) the excitation wavelengths and (b) the emission wavelengths of the fluorescent agents shift toward longer wavelengths approaching the bottom of the stack.

38. The method of claim 35 including a further step of forming anti-reflective interfaces between the layers.

39. The method of claim 38 in which the step of forming anti-reflective interfaces includes forming diffuse interfaces between the layers.

40. The method of claim 38 in which the step of forming anti-reflective interfaces includes forming refractive-index matching joints between the layers.

41. The method of claim 35 further comprising a step of appending an opaque layer to the bottom of the stack.

42. The method of claim 41 in which the step of appending an opaque layer includes forming the opaque layer from a diffusely reflective material.

\* \* \* \* \*